(12) United States Patent
Schelberger et al.

(10) Patent No.: US 6,903,108 B2
(45) Date of Patent: Jun. 7, 2005

(54) FUNGICIDAL MIXTURES BASED ON AMIDE COMPOUNDS AND PYRIDINE DERIVATIVES

(75) Inventors: Klaus Schelberger, Gönnheim (DE); Maria Scherer, Landau (DE); Karl Eicken, Wachenheim (DE); Manfred Hampel, Neustadt (DE); Eberhard Ammermann, Heppenheim (DE); Gisela Lorenz, Neustadt (DE); Siegfried Strathmann, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 163 days.

(21) Appl. No.: 10/044,255

(22) Filed: Jan. 14, 2002

(65) Prior Publication Data

US 2003/0036480 A1 Feb. 20, 2003

Related U.S. Application Data

(62) Division of application No. 09/581,833, filed as application No. PCT/EP98/08231 on Dec. 15, 1998, now Pat. No. 6,365,608.

(30) Foreign Application Priority Data

Dec. 18, 1997 (DE) .......................... 197 56 379

(51) Int. Cl.[7] ...................... A61K 31/505; A61K 31/44; C07D 213/56; C07D 239/02; C07D 209/04
(52) U.S. Cl. ...................... 514/275; 514/277; 514/347; 514/348; 544/330; 546/316; 548/469; 548/570
(58) Field of Search ................. 544/330; 546/316; 514/275, 277, 347, 348; 548/469, 570

(56) References Cited

U.S. PATENT DOCUMENTS

| 4,092,422 | A | | 5/1978 | Mayr et al. ............... 424/270 |
|---|---|---|---|---|
| 4,803,214 | A | | 2/1989 | Brandes et al. ............ 514/383 |
| 5,330,995 | A | | 7/1994 | Eicken et al. ............. 514/355 |
| 5,521,184 | A | * | 5/1996 | Zimmermann ......... 514/252.11 |
| 5,877,201 | A | | 3/1999 | Ammermann et al. ...... 514/417 |
| 6,130,224 | A | | 10/2000 | Eicken et al. ............. 514/259 |
| 6,262,091 | B1 | | 7/2001 | Wagner et al. ............. 514/355 |
| 6,365,608 | B1 | * | 4/2002 | Schelberger et al. ........ 514/352 |

FOREIGN PATENT DOCUMENTS

| CA | 2230140 | 3/1997 |
|---|---|---|
| EP | 0 209 234 | 1/1987 |
| EP | 0 256 503 | 2/1988 |
| EP | 531116 B1 | 5/1995 |
| EP | 0 545 099 | 6/1999 |
| JP | 02/196701 | 1/1989 |
| JP | 2196701 | 8/1990 |
| WO | WO 97/08952 | 3/1997 |
| WO | WO 97/39628 | 10/1997 |

OTHER PUBLICATIONS

Falloon et al., "Seedling of marrow stem kale controlled with fungicide seed treat–ments"; Abstract of Proc. NZ Weed Pest Control Conf. 39, 49–53 (1986).

* cited by examiner

Primary Examiner—Cecilia J. Tsang
Assistant Examiner—Binta Robinson
(74) Attorney, Agent, or Firm—Keil & Weinkauf

(57) ABSTRACT

Fungicidal mixtures comprise as active components
  a) an amide compound of the formula I $$A-CO-NR^1R^2 \qquad\qquad I$$

in which
A is an aryl group or an aromatic or non-aromatic, 5- or 6-membered heterocycle which has from 1 to 3 hetero atoms selected from O, N and S;
  where the aryl group or the heterocycle may or may not have 1, 2 or 3 substituents which are selected, independently of one another, from alkyl, halogen, $CHF_2$, $CF_3$, alkoxy, haloalkoxy, alkylthio, alkylsulfynyl and alkylsulfonyl;
$R^1$ is a hydrogen atom;
$R^2$ is a phenyl or cycloalkyl group which may or may not have 1, 2 or 3 substituents which are selected, independently of one another, from alkyl, alkenyl, alkynyl, alkoxy, alkenyloxy, alkynyloxy, cycloalkyl, cycloalkenyl, cycloalkyloxy, cycloalkenyloxy, phenyl and halogen, where the aliphatic and cycloaliphatic radicals may be partially or fully halogenated and/or the cycloaliphatic radicals may be substituted by from 1 to 3 alkyl groups and where the phenyl group may have from 1 to 5 halogen atoms and/or from 1 to 3 substituents which are selected, independently of one another, from alkyl, haloalkyl, alkoxy, haloalkoxy, alkylthio and haloalkylthio, and where the amidic phenyl group may or may not be condensed with a saturated 5-membered ring which may or may not be substituted by one or more alkyl groups and/or may have a hetero atom selected from O and S, and and [sic]
b) fungicides from the group of the dicarboximides and/or
c) pyrimidine derivatives of the formula III:

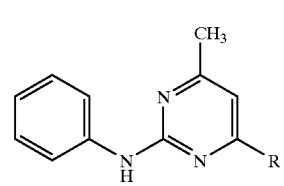

in which R is methyl, propyn-1-yl or cyclopropyl, and/or
d) fludioxinil or fenpiclonil and/or
e) captan, captafol or folpet and/or
f) fluazinam and/or
g) dichlofluanid or tolylfluanid
in a synergistically effective amount.

16 Claims, No Drawings

FUNGICIDAL MIXTURES BASED ON AMIDE COMPOUNDS AND PYRIDINE DERIVATIVES

This is a Divisional application of application Ser. No. 09/581,833, filed on Jun. 19, 2000 (U.S. Pat. No. 6,365,608 B1) which is a 371 of PCT/EB98/08231 filed Dec. 15, 1998.

The present invention relates to fungicidal mixtures for controlling harmful fungi, which mixtures comprise amide compounds of the formula I

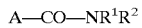  (I)

in which

A is an aryl group or an aromatic or non-aromatic, 5- or 6-membered heterocycle which has from 1 to 3 hetero atoms selected from O, N and S;
where the aryl group or the heterocycle may or may not have 1, 2 or 3 substituents which are selected, independently of one another, from alkyl, halogen, $CHF_2$, $CF_3$, alkoxy, haloalkoxy, alkylthio, alkylsulfynyl and alkylsulfonyl;

$R^1$ is a hydrogen atom;

$R^2$ is a phenyl or cycloalkyl group which may or may not have 1, 2 or 3 substituents which are selected from alkyl, alkenyl, alkynyl, alkoxy, alkenyloxy, alkynyloxy, cycloalkyl, cycloalkenyl, cycloalkyloxy, cycloalkenyloxy, phenyl and halogen, where the aliphatic and cycloaliphatic radicals may be partially or fully halogenated and/or the cycloaliphatic radicals may be substituted by from 1 to 3 alkyl groups and where the phenyl group may have from 1 to 5 halogen atoms and/or from 1 to 3 substituents which are selected, independently of one another, from alkyl, haloalkyl, alkoxy, haloalkoxy, alkylthio and haloalkylthio, and where the amidic phenyl group may or may not be condensed with a saturated 5-membered ring which may or may not be substituted by one or more alkyl groups and/or may have a hetero atom selected from O and S, and b) fungicides of the group of the dicarboximides and/or c) a pyrimidine derivative of the formula III,

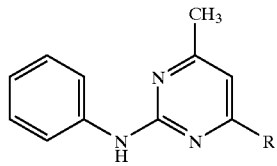  III in which R is methyl, propyn-1-yl or cyclopropyl, and/or d) at least one active ingredient of the formula IV or V,

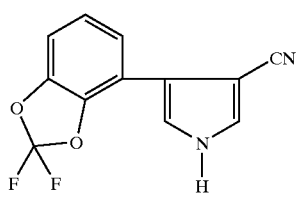  IV

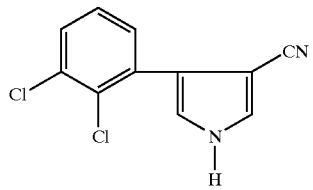  V and/or e) a phthalimide derivative selected from the group consisting of the compounds VIa, VIb and VII:

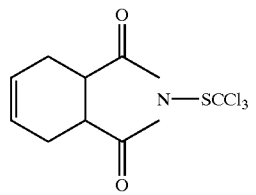  VIa

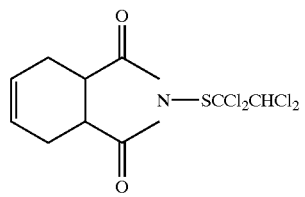  VIb

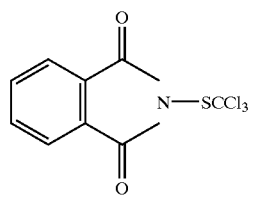  VII and/or f) a dinitroaniline of the formula VIII:

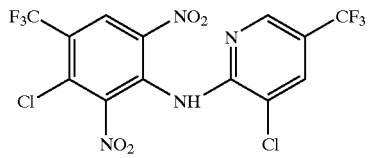  VIII and/or g) an arylsulfamide of the formula IX a or IXb:

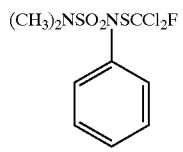  IXa

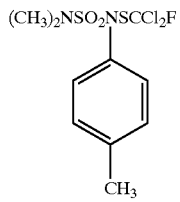
IXb in a synergistically effective amount.

WO 97/08952 describes fungicidal mixtures which, in addition to compounds of the formula I, also comprise fenazaquin as further components. These are described as being very effective against *Botrytis*.

The amide compounds of the formula I are known per se and are described in the literature (EP-A 545 099).

Fungicides from the group of the dicarboximides are known to the person skilled in the art and are commercially available.

Also known are the pyrimidine derivatives III, their preparation and their activity against harmful fungi [R=methyl: DD-A 151 404 (common name: pyrimethanil); R=1-propynyl: EP-A 224 339 (common name: mepanipyrim); R=cyclopropyl: EP-A 310 550].

The compound IV is known from K. Gehmann, R. Nyfeler, A. J. Leadbeater, D. Nevill and D. Sozzi, Proceedings of the Brighton Crop Protection Conference, Pests and Diseases 1990, Vol. 2, p. 399 (common name: fludioxinil) and is commercially available from Novartis.

The compound V is known from D. Nevill, R. Nyfeler, D. Sozzi, Proceedings of the Brighton Crop Protection Conference, Pests and Diseases 1988, Vol. 1, p. 65 (common name: fenpiclonil).

U.S. Pat. Nos. 2,553,770; 2,553,771; 2,553,776 describe the compounds VIa (common name: captan) and VII (common name: folpet), their preparation and their activity against harmful fungi. The compound VIb (common name: captafol) is described in Phytopathology 52(1962), 52, 754.

Likewise, the compound VIII, its preparation and its use (CAS RN 79622-59-6, common name: fluazinam) are described in the literature.

The compounds IXa and IXb are known under the common names dichlofluanid and tolylfluanid, respectively, and are described in the German patent 1193498.

It is an object of the present invention to provide mixtures which have an improved activity against harmful fungi combined with a reduced total amount of active ingredients applied (synergistic mixtures), with a view to reducing the application rates and to improving the activity spectrum of the known compounds.

We have found that this object is achieved by the mixtures defined at the outset. Moreover, we have found that better control of harmful fungi is possible by applying the compounds I and the compounds II to VIII simultaneously, that is either together or separately, or by applying the compounds I and the compounds II to VIII in succession than when the compounds I or II to VIII are applied on their own.

The mixtures according to the invention have synergistic action and are therefore particularly suitable for controlling harmful fungi, in particular of *Botrytis* species.

In the context of the present invention, halogen is fluorine, chlorine, bromine and iodine and is in particular fluorine, chlorine and bromine.

The term "alkyl" includes straight-chain and branched alkyl groups. These are preferably straight-chain or branched $C_1$–$C_{12}$-alkyl and in particular $C_1$–$C_6$-alkyl groups. Examples of alkyl groups are alkyl such as, in particular, methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 1-ethylpentyl, 2-ethylpentyl, 1-propylbutyl, octyl, decyl, dodecyl.

Haloalkyl is an alkyl group as defined above which is partially or fully halogenated by one or more halogen atoms, in particular by fluorine and chlorine. Preferably, there are from 1 to 3 halogen atoms present, and the difluoromethyl or the trifluoromethyl group is particularly preferred.

The above statements for the alkyl group and the haloalkyl group apply in a corresponding manner to the alkyl and haloalkyl groups in alkoxy, haloalkoxy, alkylthio, haloalkylthio, alkylsulfynyl and alkylsulfonyl.

The alkenyl group includes straight-chain and branched alkenyl groups. These are preferably straight-chain or branched $C_3$–$C_{12}$-alkenyl groups and in particular $C_3$–$C_6$-alkenyl groups. Examples of alkenyl groups are 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-dimethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl and 3-methyl-2-pentenyl.

The alkenyl group may be partially or fully halogenated by one or more halogen atoms, in particular by fluorine or chlorine. The alkenyl group preferably has from 1 to 3 halogen atoms.

The alkynyl group includes straight-chain and branched alkynyl groups. These are preferably straight-chain and branched $C_3$–$C_{12}$-alkynyl groups and in particular $C_3$–$C_6$-alkynyl groups. Examples of alkynyl groups are 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,2-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl.

The above statements for the alkenyl group and its halogen substituents and for the alkynyl group apply in a corresponding manner to alkenyloxy and alkynyloxy.

The cycloalkyl group is preferably a $C_3$–$C_6$cycloalkyl group, such as cyclopropyl, cyclobutyl, cyclopentyl or cyclohexyl. If the cycloalkyl group is substituted, it preferably has from 1 to 3 $C_1$–$C_4$-alkyl radicals as substituents.

Cycloalkenyl is preferably a $C_4$–$C_6$-cycloalkenyl group, such as cyclobutenyl, cyclopentenyl or cyclohexenyl. If the cycloalkenyl group is substituted, it preferably has from 1 to 3 $C_1$–$C_4$-alkyl radicals as substituents.

A cycloalkoxy group is preferably a $C_5$–$C_6$-cycloalkoxy group, such as cyclopentyloxy or cyclohexyloxy. If the cycloalkoxy group is substituted, it preferably has from 1 to 3 $C_1$–$C_4$-alkyl radicals as substituents.

The cycloalkenyloxy group is preferably a $C_5$–$C_6$-cycloalkenyloxy group, such as cyclopentyloxy or cyclohexyloxy. If the cycloalkenyloxy group is substituted, it preferably has from 1 to 3 $C_1$–$C_4$-alkyl radicals as substituents.

Aryl is preferably phenyl.

If A is a phenyl group, this may have one, two or three of the abovementioned substituents in any position. These substituents are preferably selected, independently of one another, from alkyl, difluoromethyl, trifluoromethyl and halogen, in particular chlorine, bromine and iodine. Particularly preferably, the phenyl group has a substituent in the 2-position.

If A is a 5-membered heterocycle, it is in particular a furyl, thiazolyl, pyrazolyl, imidazolyl, oxazolyl, thienyl, triazolyl or thiadiazolyl radical or the corresponding dihydro or tetrahydro derivatives thereof. Preference is given to a thiazolyl or pyrazolyl radical.

If A is a 6-membered heterocycle, it is in particular a pyridyl radical or a radical of the formula:

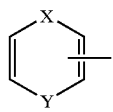

in which one of the radicals X and Y is O, S or $NR^{23}$, where $R^{23}$ is H or alkyl, and the other of the radicals X and Y is $CH_2$, S, SO, $SO_2$ or $NR^{23}$. The dotted line means that a double bond may or may not be present.

The 6-membered aromatic heterocycle is particularly preferably a pyridyl radical, in particular a 3-pyridyl radical, or a radical of the formula:

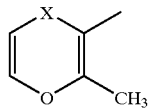
(A3)

in which X is $CH_2$, S, SO or $SO_2$.

The abovementioned heterocyclic radicals may or may not have 1, 2 or 3 of the abovementioned substituents, where these substituents are preferably selected, independently of one another, from alkyl, halogen, difluoromethyl or trifluoromethyl.

A is particularly preferably a radical of the formulae:

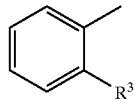
(A1)

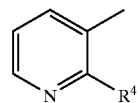
(A2)

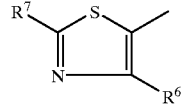
(A5)

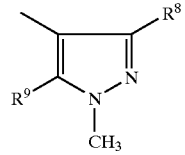
(A7)

in which $R^3$, $R^4$, $R^6$, $R^7$, $R^8$ and $R^9$ independently of one another are hydrogen, alkyl, in particular methyl, halogen, in particular chlorine, $CHF_2$ or $CF_3$.

The radical $R^1$ in the formula I is preferably a hydrogen atom.

The radical $R^2$ in the formula I is preferably a phenyl radical. $R^2$ preferably has at least one substituent which is particularly preferably in the 2-position. The substituent (or the substituents) is (are) preferably selected from the group consisting of alkyl, cycloalkyl, cycloalkenyl, halogen or phenyl.

The substituents of the radical $R^2$ may in turn be substituted again. The aliphatic or cycloaliphatic substituents may be partially or fully halogenated, in particular fluorinated or chlorinated. They preferably have 1, 2 or 3 fluorine or chlorine atoms. If the substituent of the radical $R^2$ is a phenyl group, this phenyl group may preferably be substituted by from 1 to 3 halogen atoms, in particular chlorine atoms, and/or by a radical which is preferably selected from alkyl and alkoxy. Particularly preferably, the phenyl group is substituted with a halogen atom in the p-position, i.e. the particularly preferred substituent of the radical $R^2$ is a p-halogen-substituted phenyl radical. The radical $R^2$ may also be condensed with a saturated 5-membered ring, where this ring for its part may have from 1 to 3 alkyl substituents.

$R^2$ is in this case, for example, indanyl, thiaindanyl and oxaindanyl. Preference is given to indanyl and 2-oxaindanyl which are attached to the nitrogen atom in particular via the 4-position.

According to a preferred embodiment, the composition according to the invention comprises as amide compound a compound of the formula I in which A is as defined below:
phenyl, pyridyl, dihydropyranyl, dihydrooxathiynyl, dihydrooxathiynyloxide, dihydrooxathiynyldioxide, furyl, thiazolyl, pyrazolyl or oxazolyl, where these groups may have 1, 2 or 3 substituents which are selected, independently of one another, from alkyl, halogen, difluoromethyl and trifluoromethyl.

According to a further preferred embodiment, A is one of the following groups:
pyridin-3-yl, which may or may not be substituted in the 2-position by halogen, methyl, difluoromethyl, trifluoromethyl, methoxy, methylthio, methylsulfynyl or methylsulfonyl;
phenyl, which may or may not be substituted in the 2-position by methyl, trifluoromethyl, chlorine, bromine or iodine;
2-methyl-5,6-dihydropyran-3-yl;
2-methyl-5,6-dihydro-1,4-oxathiyn-3-yl or the 4-oxide or 4,4-dioxide thereof;

2-methylfuran-3-yl, which may or may not be substituted in the 4- and/or 5-position by methyl;
thiazol-5-yl, which may or may not be substituted in the 2- and/or 4-position by methyl, chlorine, difluoromethyl or trifluoromethyl;
thiazol-4-yl, which may or may not be substituted in the 2- and/or 5-position by methyl, chlorine, difluoromethyl or trifluoromethyl;
1-methylpyrazol-4-yl, which may or may not be substituted in the 3- and/or 5-position by methyl, chlorine, difluoromethyl or trifluoromethyl; or
oxazol-5-yl, which may or may not be substituted in the 2- and/or 4-position by methyl or chlorine.

According to a further preferred embodiment, the compositions according to the invention comprise as amide compound a compound of the formula I in which $R^2$ is a phenyl group which may or may not be substituted by 1, 2 or 3 of the above-mentioned substituents.

According to a further preferred embodiment, the compositions according to the invention comprise as amide compound a compound of the formula I in which $R^2$ is a phenyl group which has one of the following substituents in the 2-position:

$C_3$–$C_6$-alkyl, $C_5$–$C_6$-cycloalkenyl, $C_5$–$C_6$-cycloalkyloxy, cycloalkenyloxy, where these groups may be substituted by 1, 2 or 3 $C_1$–$C_4$-alkyl groups,
phenyl, which is substituted by from 1 to 5 halogen atoms and/or from 1 to 3 groups which are selected, independently of one another, from $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio,
indanyl or oxaindanyl which may or may not be substituted by 1, 2 or 3 $C_1$–$C_4$-alkyl groups.

According to a further preferred embodiment, the compositions according to the invention comprise as amide compound a compound of the formula Ia,

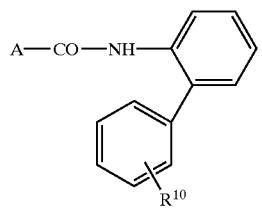
(Ia)

in which
A is

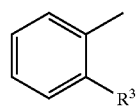
(A1)

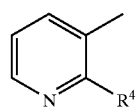
(A2)

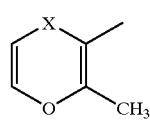
(A3)

-continued

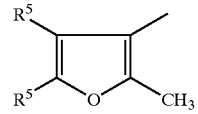
(A4)

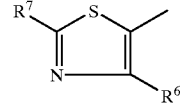
(A5)

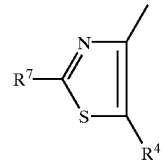
(A6)

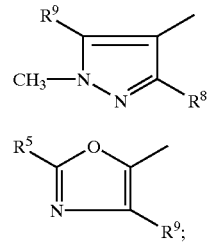
(A7)
(A8)

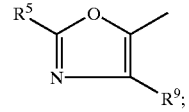

X is methylene, sulfur, sulfynyl or sulfonyl ($SO_2$),
$R^3$ is methyl, difluoromethyl, trifluoromethyl, chlorine, bromine or iodine,
$R^4$ is trifluoromethyl or chlorine,
$R^5$ is hydrogen or methyl,
$R^6$ is methyl, difluoromethyl, trifluoromethyl or chlorine,
$R^7$ is hydrogen, methyl or chlorine,
$R^8$ is methyl, difluoromethyl or trifluoromethyl,
$R^9$ is hydrogen, methyl, difluoromethyl, trifluoromethyl or chlorine,
$R^{10}$ is $C_1$–$C_4$-alkyl, $C_1$–$C_4$-alkoxy, $C_1$–$C_4$-alkylthio or halogen.

According to a particularly preferred embodiment, the compositions comprise as amide compound a compound of the formula Ib:

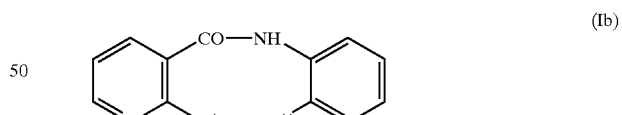
(Ib)

in which
$R^4$ is halogen and
$R^{11}$ is phenyl which is substituted by halogen.

Useful amide compounds of the formula I are mentioned in EP-A-545 099 and 589 301 which are incorporated herein in their entirety by reference.

The preparation of the amide compounds of the formula I is known, for example, from EP-A-545 099 or 589 301 or can be carried out by similar processes.

Preferred substituents $R^{21}$ and $R^{22}$ are hydrogen, F, Cl, methyl, ethyl, methoxy, thiomethyl and N-methylamino. $R^3$ and $R^4$ together may also form a grouping =O.

Preferred fungicides of the dicarboximide type are the compounds IIa to IId:

II.a: ethyl (RS)-3-(3,5-dichlorophenyl)-5-methyl-2,4-dioxooxazolidine-5-carboxylate

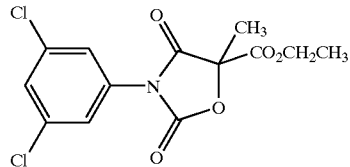

II.a

II.b: 3-(3,5-dichlorophenyl)-N-isopropyl-2,4-dioxoimidazolidine-1-carboxamide

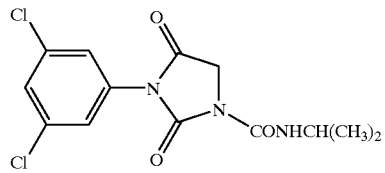

II.b

II.c: N-(3,5-dichlorophenyl)-1,2-dimethylcyclopropane-1,2-dicarboximide

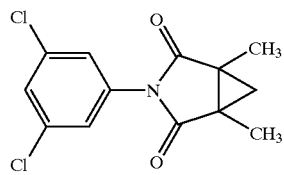

II.c

II.d: (RS)-3-(3,5-dichlorophenyl)-5-ethenyl-5-methyl-1,3-oxazolidine-2,4-dione

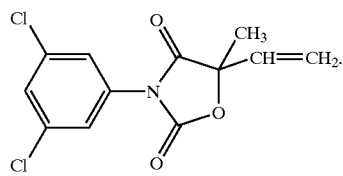

II.d

These compounds are commercially available as fungicidally active ingredients and are described in the literature as follows:

II.a (common name: chlozolinate): CAS RN [84332-86-5], DE-A 29 06 574;

II.b (common name: iprodione): CAS RN [36734-19-7], U.S. Pat. No. 3,755,350;

II.c (common name: procymidone): CAS RN [32809-16-8], U.S. Pat. No. 3,903,090;

II.d (common name: vinclozoline): CAS RN [50471-44-8), DE-A 22 07 576].

To unfold the synergistic activity, even a small amount of the amide compound of the formula I is sufficient. Preference is given to employing amide compound and active ingredient of the formula II and/or III to IX in a weight ratio in the range of from 50:1 to 1:50, in particular from 10:1 to 1:10. It is also possible here to employ ternary mixtures which, in addition to amide compounds I, comprise both compounds II and one or more compounds III to IX. In such mixtures, the mixing ratio of the compounds II and III to IX with each other is usually in the range of from 50:1 to 1:50, preferably from 10:1 to 1:10.

Owing to the basic character of their nitrogen atoms, the compounds III, IV, V and VIII are capable of forming salts or adducts with inorganic or organic acids or with metal ions.

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid and alkanoic acids, such as acetic acid, trifluoroacetic acid, trichicroacetic acid and propionic acid, and also glycolic acid, thiocyanic acid, lactic acid, succinic acid, citric acid, benzoic acid, cinnamic acid, oxalic acid, alkylsulfoflic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfo groups), alkylphosphoflic acids (phosphonic acids having straight-chain or branched alkyl radicals of 1 to 20 carbon atoms), arylphosphonic acids or aryldiphosphoflic acids (aromatic radicals, such as phenyl and naphthyl, which carry one or two phosphonic acid radicals), it being possible for the alkyl or aryl radicals to carry further substituents, eg. p-toluenesulfonic acid, salicylic acid, p-aminosalicylic acid, 2-phenoxybenzoic acid, 2-acetoxybenzoic acid, etc.

Suitable metal ions are, in particular, the ions of the elements of the first to eighth sub-group, in particular chromium, manganese, iron, cobalt, nickel, copper, zinc and furthermore of the second main group, in particular calcium and magnesium, and of the third and fourth main group, in particular aluminum, tin and lead. The metals can exist in the various valencies which they can assume.

When preparing the mixtures, it is preferred to employ the pure active ingredients I and II to IX, to which further active ingredients against harmful fungi or other pests, such as insects, arachnids or nematodes, or else herbicidal or growth-regulating active ingredients or fertilizers, can be admixed.

The mixtures of the compounds I and II and/or III to IX, or the compounds I and II and/or III to IX used simultaneously, jointly or separately, exhibit outstanding activity against a wide range of phytopathogenic fungi, in particular from the classes of the Ascomycetes, Basidiomycetes, Phycomycetes and Deuteromycetes. Some of them act systemically and can therefore be employed as foliar- and soil-acting fungicides.

They are especially important for controlling a large number of fungi in a variety of crop plants, such as cotton, vegetable species (eg. cucumbers, beans, tomatoes, potatoes and cucurbits), barley, grass, oats, bananas, coffee, maize, fruit species, rice, rye, soya, grapevine, wheat, ornamentals, sugar cane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, *Puccinia* species in cereals, *Rhizoctonia* species in cotton, rice and lawns, *Ustilago* species in cereals and sugar cane, *Venturia inaequalis* (scab) in apples, *Helminthosporium* species in cereals, *Septoria nodorum* in wheat, *Botrytis cinerea* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapevines, *Pseudoperonospora* species in hops and cucumbers, *Alternaria* species in vegetables and fruit, *Hycosphaerella* species in bananas and *Fusarium* and *Verticillium* species.

The mixtures according to the invention may particularly preferably be employed for controlling Botrytis species in crops of grapevines and vegetables, and also in ornamentals.

The compounds I and II and/or III to IX can be applied simultaneously, either together or separately, or in succession, the sequence, in the case of separate application, generally not having any effect on the result of the control measures.

Depending on the kind of effect desired, the application rates of the mixtures according to the invention are, in particular in agricultural crop areas, from 0.01 to 8 kg/ha, preferably 0.1 to 5 kg/ha, in particular 0.2 to 3.0 kg/ha.

The application-rates of the compounds I are from 0.01 to 2.5 kg/ha, preferably 0.05 to 2.5 kg/ha, in particular 0.1 to 1.0 kg/ha.

Correspondingly, in the case of the compounds II and/or III to IX, the application rates are from 0.01 to 10 kg/ha, preferably 0.05 to 5 kg/ha, in particular 0.05 to 2.0 kg/ha.

For seed treatment, the application rates of the mixture are generally from 0.001 to 250 g/kg of seed, preferably 0.01 to 100 g/kg, in particular 0.01 to 50 g/kg.

If phytopathogenic harmful fungi are to be controlled, the separate or joint application of the compounds I and II and/or III to IX or of the mixtures of the compounds I and II and/or III to IX is effected by spraying or dusting the seeds, the plants or the soils before or after sowing of the plants, or before or after plant emergence.

The fungicidal synergistic mixtures according to the invention, or the compounds I and II and/or III to IX, can be formulated for example in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform as possible a distribution of the mixture according to the invention.

The formulations are prepared in a known manner, eg. by extending the active ingredient with solvents and/or carriers, if desired using emulsifiers and dispersants, it being possible also to use other organic solvents as auxiliary solvents if water is used as the diluent. Suitable auxiliaries for this purpose are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. finely divided silica, silicates); emulsifiers such as nonionic and anionic emulsifiers (eg. polyoxyethylene fatty alcohol ethers, alkylsulfonates and arylsulfonates) and dispersants such as lignosulfite waste liquors and methylcellulose.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or jointly grinding the compounds I or II and/or III to IX, or the mixture of the compounds I and II and/or III to IX, with a solid carrier.

Granules (eg. coated granules, impregnated granules or homogeneous granules) are usually prepared by binding the active ingredient, or active ingredients, to a solid carrier.

Fillers or solid carriers are, for example, mineral earths, such as silicas, silica gels, silicates, talc, kaolin, limestone, lime, chalk, bole, bess, clay, dolomite, diatomaceous earth, calcium sulfate, magnesium sulfate, magnesium oxide, ground synthetic materials and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably 0.5 to 90% by weight, of one of the compounds I and II and/or III to IX or of the mixture of the compounds I and II and/or III to IX. The active ingredients are employed in a purity of from 90% to 100%, preferably 95% to 100% (according to NMR spectrum or HPLC).

The compounds I and II and/or III to IX, the mixtures, or the corresponding formulations, are applied by treating the harmful fungi, their habitat, or the plants, seeds, soils, areas, material or spaces to be kept free from them with a fungicidally effective amount of mixture, or of the compounds I and II and/or III to IX in the case of separate application.

Application can be effected before or after infection by the harmful fungi.

Examples of such preparations comprising the active ingredients are:

I. A solution of 90 parts by weight of the active ingredients and 10 parts by weight of N-methylpyrrolidone; this solution is suitable for use in the form of microdrops;

II. A mixture of 20 parts by weight of the active ingredients, 80 parts by weight of xylene, 10 parts by weight of the adduct of 8 to 10 mol of ethylene oxide to 1 of oleic acid N-monoethanolamide, 5 parts by weight of the calcium salt of dodecylbenzenesulfonate, 5 parts by weight of the adduct of 40 mol of ethylene oxide and 1 mol of castor oil; a dispersion is obtained by finely distributing the solution in water;

III. An aqueous dispersion of 20 parts by weight of the active ingredients, 40 parts by weight of cyclohexanone, 30 parts by weight of isobutanol, 20 parts by weight of the adduct of 40 mol of ethylene oxide and 1 mol of castor oil;

IV. An aqueous dispersion of 20 parts by weight of the active ingredients, 25 parts by weight of cyclohexanone, 65 parts by weight of a mineral oil fraction of boiling point 210 to 280° C., and 10 parts by weight of the adduct of 40 mol of ethylene oxide and 1 mol of castor oil;

V. A mixture, ground in hammer mill, of 80 parts by weight of active ingredients, 3 parts by weight of the sodium salt of diisobutylnaphtalene-1-sulfonate, 10 parts by weight of the sodium salt of a lignosulfonic acid from a silica gel; a spray mixture is obtained by finely distributing the mixture in water;

VI. A intimate mixture of 3 parts by weight of the active ingredients and 97 parts by weight of finely divided kaolin; this dust comprises 3% by weight of active ingredients;
VII. An intimate mixture of 30 parts by weight of the active ingredients, 92 parts by weight of pulverulent silica gel and 8 parts by weight of paraffin oil which had been sprayed onto the surface of this silica gel; this formulation imparts good adhesion to the active ingredient;
VIII. A stable aqueous dispersion of 40 parts by weight of the active ingredients, 10 parts by weight of the sodium salt of a phenolsulfonic acid/urea/formaldehyde condensate, 2 parts by weight of silica gel and 48 parts by weight of water; this dispersion may be diluted further;
IX. A stable oily dispersion of 20 parts by weight of the active ingredients, 2 parts by weight of the calcium salt of dodecylbenzenesulfonate, 8 parts by weight of fatty alcohol polyglycol ether, 20 parts by weight of the sodium salt of a phenolsulfonic acid/urea/formaldehyde condensate and 88 parts by weight of a paraffinic mineral oil.

USE EXAMPLE

The synergistic activity of the mixtures according to the invention can be demonstrated by the following experiments:

The active ingredients, separately or together, are formulated as a 10% emulsion in a mixture of 63% by weight of cyclohexanone and 27% by weight of emulsifier, and diluted with water to the desired concentration.

Evaluation is carried out by determining the infected leaf areas in percent. These percentages are converted into efficacies. The efficacy (w) is calculated as follows using Abbot's formula:

$$W=(1-\alpha)\cdot 100/\beta$$

α corresponds to the fungal infection of the treated plants in % and
β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active ingredients were determined using Colby's formula [R. S. Colby, Weeds 15, 20–22 (1967)] and compared with the observed efficacies.

Colby formula: $E=x+y-x\cdot y/100$

E expected efficacy, expressed in % of the untreated control, when using the mixture of the active ingredients A and B at the concentrations a and b
x efficacy, expressed in % of the untreated control, when using active ingredient A at a concentration of a
y efficacy, expressed in % of the untreated control, when using active ingredient B at a concentration of b Use Example 1

Activity Against *Botrytis cinerea* on Bell Pepper Leaves

Bell pepper seedlings of the variety "Neusiedler Ideal Elite" were, after 4–5 leaves were well developed, sprayed to runoff point with an aqueous preparation of active ingredient which had been prepared from a stock solution comprising 10% of active ingredient, 63% of cyclohexanone and 27% of emulsifier. The next day, the treated plants were inoculated with a spore suspension of *Botrytis cinerea* containing $1.7\times10^6$ spores per ml of a 2% strength aqueous Biomalz solution. The test plants were subsequently placed in a climatized chamber with high atmospheric humidity at 22–24° C. After 5 days, the extent of the fungal infection on the leaves could be determined visually in %.

The compounds of the formula I used were the following components:

I.1

I.2

The results are shown in Tables 1 and 2 below.

TABLE 1

| Ex. | Active ingredient | Concentration of active ingredient in the spray liquor in ppm | Efficacy in % of the untreated control |
|---|---|---|---|
| 1C | untreated | 0 (99% infection) | 0 |
| 2C | Compound I.1 | 31 | 78 |
|  |  | 16 | 67 |
|  |  | 8 | 11 |
| 3C | Compound I.2 | 31 | 67 |
|  |  | 16 | 44 |
|  |  | 8 | 44 |
| 4C | Compound VIa | 31 | 0 |
|  |  | 16 | 0 |
|  |  | 8 | 0 |
| 5C | Compound VII | 31 | 0 |
|  |  | 16 | 0 |
|  |  | 8 | 0 |
| 6C | Compound IXa | 31 | 0 |
|  |  | 16 | 0 |
|  |  | 8 | 0 |

TABLE 2

| Ex. | Mixtures according to the invention (content in ppm) | observed efficacy | calculated efficacy*) |
|---|---|---|---|
| 7 | 31 ppm I.1 + 31 ppm VIa | 97 | 78 |
| 8 | 8 ppm I.1 + 8 ppm VIa | 30 | 11 |
| 9 | 31 ppm I.2 + 31 ppm VIa | 100 | 67 |
| 10 | 16 ppm I.2 + 16 ppm VIa | 70 | 44 |
| 11 | 31 ppm I.1 + 31 ppm VII | 90 | 78 |

TABLE 2-continued

| Ex. | Mixtures according to the invention (content in ppm) | observed efficacy | calculated efficacy* |
|---|---|---|---|
| 12 | 8 ppm I.1 + 8 ppm VII | 39 | 11 |
| 13 | 31 ppm I.2 + 31 ppm VII | 93 | 67 |
| 14 | 16 ppm I.2 + 16 ppm VII | 90 | 44 |
| 15 | 8 ppm I.2 + 8 ppm VII | 90 | 44 |
| 16 | 31 ppm I.1 + 31 ppm IXa | 95 | 78 |
| 17 | 16 ppm I.1 + 16 ppm IXa | 90 | 67 |
| 18 | 31 ppm I.2 + 31 ppm IXa | 100 | 67 |
| 19 | 16 ppm I.2 + 16 ppm IXa | 99 | 44 |
| 20 | 8 ppm I.2 + 8 ppm IXa | 90 | 44 |

*)calculated using Colby's formula

The test results show that for all mixing ratios the observed efficacy is higher than the efficacy which had been calculated beforehand using Colby's formula.

Use Example 2

Activity Against *Botryis Cinerea* on Bell Peppers

Disks of green bell peppers were sprayed to runoff point with an aqueous preparation of active ingredient which had been prepared from a stock solution comprising 10% of active ingredient, 63% of cyclohexanone and 27% of emulsifier. 2 hours after the spray coating had dried on, the fruit disks were inoculated with a spore suspension of *Botrytis cinerea* containing $1.7 \times 10^6$ spores per ml of a 2% strength Biomalz solution. The inoculated fruit disks were subsequently incubated in humid chambers at 18° C. for 4 days. The *Botrytis* infection on the diseased fruit disks was then evaluated visually.

The result are shown in Tables 3 and 4 below.

TABLE 3

| Ex. | Active ingredient | Concentration of active ingredient in the spray liquor in ppm | Efficacy in % of the untreated control |
|---|---|---|---|
| 21C | untreated | 0 (100% infection) | 0 |
| 22C | Compound I.1 | 31 | 0 |
|  |  | 16 | 0 |
| 23C | Compound I.2 | 31 | 20 |
|  |  | 16 | 0 |
| 24C | Compound IV | 31 | 0 |
|  |  | 16 | 0 |
| 25C | Compound VIa | 31 | 0 |
| 26C | Compound VII | 31 | 0 |
| 27C | Compound VIII | 31 | 0 |
|  |  | 16 | 0 |

TABLE 4

| Ex. | Mixtures according to the invention (content in ppm) | observed efficacy | calculated efficacy* |
|---|---|---|---|
| 28 | 31 ppm I.1 + 31 ppm IV | 50 | 0 |
| 29 | 16 ppm I.1 + 16 ppm IV | 20 | 0 |
| 30 | 31 ppm I.2 + 31 ppm IV | 70 | 20 |
| 31 | 16 ppm I.2 + 16 ppm IV | 20 | 0 |
| 32 | 31 ppm I.2 + 31 ppm IVa | 50 | 20 |
| 33 | 31 ppm I.2 + 31 ppm VII | 40 | 20 |
| 34 | 31 ppm I.1 + 31 ppm VIII | 30 | 0 |
| 35 | 16 ppm I.2 + 16 ppm VIII | 20 | 0 |

*)calculated using Colby's formula

The test results show that for all mixing ratios the observed efficacy is higher than the efficacy which had been calculated beforehand using Colby's formula.

What is claimed is:

1. A fungicidal composition comprising, as a first active component:

a) an amide compound of formula I:

$$A\text{—}CO\text{—}NR^1R^2$$

in which

A is pyridyl which is unsubstituted or carries 1, 2 or 3 substituents selected from alkyl, halogen, $CHF_2$, $CF_3$, alkoxy, haloalkoxy, alkylthio, alkylsulfynyl and alkylsulfonyl;

$R^1$ is a hydrogen atom;

$R^2$ is phenyl which is unsubstituted or carries 1, 2 or 3 substituents selected from alkyl, alkenyl, alkynyl, alkoxy, alkenyloxy, alkynyloxy, cycloalkyl, cycloalkenyl, cycloalkyloxy, cycloalkenyloxy, phenyl and halogen, where the aliphatic and cycloaliphatic radicals are unsubstituted or are partially or fully halogenated, and the cycloaliphatic radicals optionally carry from 1 to 3 alkyl groups, and where the phenyl group is unsubstituted or carries from 1 to 5 halogen atoms and/or from 1 to 3 substituents selected from alkyl, haloalkyl, alkoxy, haloalkoxy, alkylthio and haloalkylthio;

and, as a second active component, a compound selected from the group consisting of c), d), e), f) and g), wherein:

c) is a pyrimidine compound of formula III:

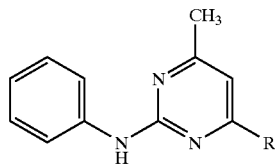

III in which R is methyl, propyn-1-yl or cyclopropyl, d) is an active ingredient of formula IV or V:

(IV) [structure: benzodioxole with CF2, connected to pyrrole-CN]

(V) [structure: 2,3-dichlorophenyl connected to pyrrole-CN]

e) is a phthalimide compound of formula VIa, VIb or VII:

(VIa) [structure: tetrahydrophthalimide-N-SCCl3]

(VIb) [structure: tetrahydrophthalimide-N-SCCl2CHCl2]

(VII) [structure: phthalimide-N-SCCl3]

f) is a dinitroaniline of formula VIII:

(VIII) [structure: F3C, NO2, Cl, NO2 substituted phenyl-NH-pyridine with CF3 and Cl]

and g) is a an arylsulfamide of formula IXa or IXb:

(IXa) [structure: phenyl-N(SO2N(CH3)2)(SCCl2F)]

(IXb) [structure: 4-methylphenyl-N(SO2N(CH3)2)(SCCl2F)]

and wherein the active components are present in synergistically effective amounts.

2. The composition defined in claim 1, wherein A is pyridyl which is unsubstituted or carries 1, 2 or 3 substituents selected from alkyl, halogen, difluoromethyl and trifluoromethyl.

3. The composition defined in claim 1, wherein A is pyridin-3-yl, which is unsubstituted or is substituted in the 2-position by halogen, methyl, difluoromethyl, trifluoromethyl, methoxy, methylthio, methylsulfynyl or methylsulfonyl.

4. The composition defined in claim 1, wherein $R^2$ is phenyl which carries 1, 2 or 3 substituents.

5. The composition defined in claim 4, wherein $R^2$ is a phenyl group which has one of the following substituents in the 2-position:
   $C_3$–$C_6$-alkyl, $C_5$–$C_6$-cycloalkenyl, $C_5$–$C_6$-cycloalkyloxy, cycloalkenyloxy, where these groups are unsubstituted or substituted by 1, 2 or 3 $C_1$–$C_4$-alkyl groups,
   phenyl which is substituted by from 1 to 5 halogen atoms and/or from 1 to 3 radicals selected from $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio.

6. The composition defined in claim 1, wherein the amide compound is a compound of formula Ia:

(Ia) [structure: A—CO—NH—biphenyl with $R^{10}$]

in which
   A is a radical A2

(A2) [structure: 3-methyl-pyridine with $R^4$ at 2-position]

$R^4$ is trifluoromethyl or chlorine, and
   $R^{10}$ is $C_1$–$C_4$-alkyl, $C_1$–$C_4$-alkoxy, $C_1$–$C_4$-alkylthio or halogen.

7. The composition defined in claim 1, wherein the amide compound is a compound of formula Ib:

(Ib) [structure: pyridine-3-CO—NH-phenyl with $R^4$ and $R^{11}$]

in which
   $R^4$ is halogen and
   $R^{11}$ is phenyl which is substituted by halogen.

8. The composition defined in claim 1, wherein the amide compound is a compound of formula:

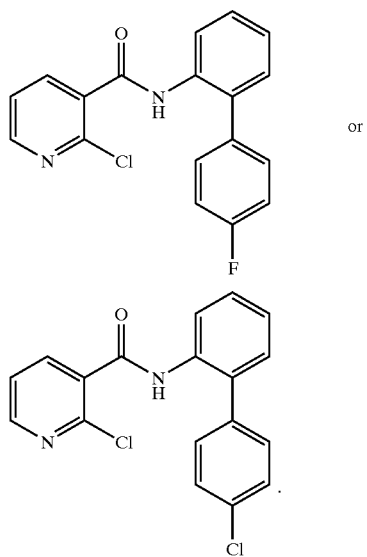

or

9. The composition defined in claim 1 specifically adapted for applying the active components simultaneously separately, or for applying the active components in succession, and having a first part comprising the amide compound of formula I in a solid or liquid carrier, and a second part comprising the second active component in a solid or liquid carrier.

10. A method for controlling harmful fungi, which comprises treating the fungi, their habitat, or materials, plants, seeds, soils, areas or spaces to be protected against fungal attack with an effective amount of the composition defined in claim 1, wherein the active components are applied simultaneously together or separately, or in succession.

11. The composition defined in claim 1, which comprises the pyrimidine compound of formula III.

12. The composition defined in claim 1, wherein the active component (a) and the second active component are present in a weight ratio of from 50:1 to 1:50.

13. The composition defined in claim 1, wherein the active component (a) and the second active component are present in a weight ratio of from 10:1 to 1:10.

14. The method of claim 10, wherein the composition comprises the pyrimidine compound of formula III.

15. The method of claim 10, wherein the active component (a) is applied in an amount of from 0.01 to 2.5 kg/ha.

16. The method of claim 10, wherein the second active component (b) is applied in an amount of from 0.01 to 10 kg/ha.

* * * * *